(12) United States Patent
Boone et al.

(10) Patent No.: US 7,980,244 B2
(45) Date of Patent: Jul. 19, 2011

(54) EMERGENCY PULMONARY RESUSCITATION DEVICE

(75) Inventors: Otho Boone, Doylestown, PA (US); Monica Ferrante, Conshohocken, PA (US); Mark Destefano, Collegeville, PA (US)

(73) Assignee: NeoForce Group, Inc., Ivyland, PA (US)

( * ) Notice: Subject to any disclaimer, the term of this patent is extended or adjusted under 35 U.S.C. 154(b) by 1035 days.

(21) Appl. No.: 11/779,037

(22) Filed: Jul. 17, 2007

(65) Prior Publication Data

US 2009/0020127 A1    Jan. 22, 2009

(51) Int. Cl.
*A61M 11/00* (2006.01)

(52) U.S. Cl. .............................. 128/200.24; 128/204.21

(58) Field of Classification Search ............. 128/200.24, 128/204.18, 204.21, 204.23, 204.24, 205.24, 128/205.23, 204.26

See application file for complete search history.

(56) References Cited

U.S. PATENT DOCUMENTS

| | | | |
|---|---|---|---|
| 1,157,655 A | 10/1915 | Mayer et al. | |
| 2,399,643 A | 5/1946 | Kreiselman | |
| 2,427,419 A | 9/1947 | Rausch | |
| 2,737,177 A | 3/1956 | Anklin | |
| RE24,193 E | 8/1956 | Emerson | |
| 4,196,725 A | 4/1980 | Gunderson | |
| 4,297,999 A * | 11/1981 | Kitrell | 128/205.16 |
| 4,651,731 A | 3/1987 | Vicenzi et al. | |
| 4,774,941 A | 10/1988 | Cook | |
| 4,821,713 A | 4/1989 | Bauman | |
| 4,898,174 A * | 2/1990 | Fangrow, Jr. | 128/204.24 |
| 4,941,469 A | 7/1990 | Adahan et al. | |
| 5,377,671 A * | 1/1995 | Biondi et al. | 128/204.23 |
| 5,398,676 A | 3/1995 | Press et al. | |
| 5,400,779 A | 3/1995 | De Resende et al. | |
| 5,520,170 A | 5/1996 | Laswick et al. | |
| 5,537,998 A | 7/1996 | Bauman | |
| 5,722,394 A | 3/1998 | Loescher | |
| 6,356,785 B1 | 3/2002 | Snyde et al. | |
| RE40,365 E * | 6/2008 | Kirchgeorg et al. | 128/205.22 |
| 2008/0262377 A1* | 10/2008 | Belson | 600/549 |

FOREIGN PATENT DOCUMENTS

KR    1020020040467 A    5/2002

OTHER PUBLICATIONS

FDA Draft Review Guidance for Ventilators, Jul. 1995.
FDA Draft Emergency Resuscitator Guidance, Apr. 14, 1993.
Circulation 2005; 112; IV-1-IV-203; Originally published online Nov. 28, 2005; http://circ.ahajournals.org.

* cited by examiner

*Primary Examiner* — Steven O Douglas
(74) *Attorney, Agent, or Firm* — Blank Rome LLP (57) ABSTRACT

An emergency pulmonary resuscitation device is described. The device of the present invention provides emergency breathing for use in techniques such as CPR, and is preferably capable of interaction with an automatic external defibrillator. The device is easy to operate and provides feedback so that it may be used by persons without medical training. The device also works through a simple action, making it possible for it to be inexpensively manufactured and widely disseminated.

19 Claims, 6 Drawing Sheets

FIG. 1 NeoForce EPRD Hospital/EMS Unit

FIG. 4 NeoForce EPRD Case

FIG. 8
EPRD PROCESS FLOW

FIG. 9
AED / EPRD ALGORITHM

EMERGENCY PULMONARY RESUSCITATION DEVICE

FIELD OF THE INVENTION

The present invention relates to devices for performing emergency pulmonary resuscitation.

BACKGROUND

Cardiovascular diseases and sudden cardiac arrest are a leading cause of death in North America. It is estimated by the American Heart Association that approximately 325,000 Americans die every year in cardiac events before they reach a hospital.

The technique of Cardio Pulmonary Resuscitation (CPR) was developed to allow for medical personnel and bystanders to treat persons suffering from sudden cardiac arrest. Standard CPR techniques require the delivery of both emergency breaths and chest compressions to the unconscious patient.

Original techniques for rescue breathing involve the use of mouth-to-mouth resuscitation. While mouth-to-mouth is a commonly known procedure for rescue breathing, it has several drawbacks. First, it requires the mouth of the person performing the procedure to come in direct physical contact with the mouth of the patient, which can cause the spread of disease. Second, it requires strenuous physical effort on behalf of the rescuer, especially when coupled with chest compressions, making it difficult to perform effectively for extended periods of time. Third, it is difficult, even for experienced medical personnel, to deliver consistent breaths using mouth-to-mouth, which may have deleterious consequences for the patient.

Prior art methods have attempted to overcome the risk of disease transmission during mouth-to-mouth by developing various devices that create a physical barrier between the rescuer and the patient. However, many of these devices are not 100% effective in preventing disease transmission, may interfere with the delivery of a rescue breaths and do not overcome the farther disadvantages of mouth-to-mouth listed above.

One prior art solution that eliminates the need for mouth-to-mouth altogether is the bag valve mask (BVM) resuscitation system or Ambu bag. Bag systems generally consist of some form of squeezable bag (such as a bulb or bellows) connected to a mask. When the bulb or bellows is contracted, air is forced into the patients airway, delivering a breath. An example of such a bag resuscitation system is described in U.S. Pat. No. 4,774,941 to Cook et al. Although bag systems overcome some of the drawbacks of the mouth-to-mouth technique, they have several disadvantages. First, although they may be less tiring than mouth-to-mouth techniques, constant squeezing of the bag requires substantial effort, and the person delivering emergency breathing can still quickly become fatigued. Second, as each person squeezes the bag in a different manner and as it is impossible for even an advanced user to make each squeeze identical, bag systems cannot be used to deliver consistent emergency breathing. As such, dangerously small or large breaths may be delivered, both of which may put the patient's life at risk. Further, inconsistent delivery of breaths over an extended period may cause damage to the patient's airway.

A few automatic ventilator/resuscitator systems are known in the art. However, these devices are typically designed as ventilators, meaning that they deliver continuous mechanical breathing. Also, the systems known in the art may not be portable, may have complicated control systems or may not provide the type of feedback that allows for their use by a member of the general public. Many of the ventilator/resuscitator systems known in the art are also very complicated to manufacture and use, making their widespread dissemination impractical. Further, as many of these devices function primarily as ventilators, their use is highly regulated and restricted in most countries around the world, making it nearly impossible for them to be available to the general public. See, for example, the FDA's Draft Guidance for Emergency Resuscitators dated July 1995 (available at http://www.fda.gov/cdrh/ode/500.pdf) and international standards ISO 10651-4 and ASTM 110-90.

U.S. Pat. No. 5,398,676 to Press et al. describes a ventilator with various modes, including an automatic CPR mode. However, the complexity of the device, its lack of feedback for the user and its primary function as a ventilator make its widespread use by the general public impracticable.

U.S. Pat. No. 5,520,170 to Laswick et al. describes an automatic resuscitator. However, the device offers no feedback to user to allow for tightly controlled delivery of emergency breaths, especially during CPR. The device detects breathing and switches to a demand mode if necessary. Because of the complexities of the Laswick device, and further because its mechanism of action is likely to cause it to be classified as a ventilator, the device is not suitable to widespread dissemination for use by members of the general public.

Both U.S. Pat. No. 4,651,731 to Vicenzi et al. and U.S. Pat. No. 4,941,469 to Adhan et al. describe portable ventilator systems. Because these systems are ventilators, they have the same drawbacks as described above. Further, these devices provide a backpressure in the patients airway during exhalation known as Positive End Expiratory Pressure (PEEP), which is not recommended during delivery of emergency breathing by the American Heart Association (see *Circulation*, 2005: 112: IV-48).

Accordingly, there is a need in the art for a portable resuscitation device that can not only be widely disseminated to the general public, but can further be used by members of the general public without medical training to provide safe and efficient emergency breathing.

SUMMARY OF THE INVENTION

It is an object of the present invention to provide an emergency pulmonary resuscitation device (EPRD) for providing emergency breathing. The EPRD allows for the highly controlled delivery of an emergency breath to a patient without requiring extensive effort on behalf of the caregiver. The EPRD of the present invention provides controlled volume delivery and controlled air flow rates to allow for the delivery of consistent emergency breaths in a manner highly consistent with recognized emergency breathing protocols. Because it provides such consistent and highly accurate breaths, use of the EPRD avoids the common and potentially dangerous situations wherein an emergency breath that is too large or too small is delivered.

It is an object of the present invention to provide an EPRD that is portable. The EPRD may operate from a variety of power sources, making it possible to use reliably almost anywhere.

It is an object of the present invention to provide an EPRD that can be used to deliver emergency breathing as part of a standard CPR protocol. As such, the EPRD of the present invention may be designed to interact and synchronize with an Automatic External Defibrillator (AED) or similar device.

It is a further object of the present invention to provide an EPRD that is designed for easy use by trained medical personnel, both in a hospital or doctor's office setting, or in the field.

It is a further object of the present invention to provide an EPRD that can be used by members of the general public without medical training. The EPRD of the present invention may be located in public spaces, offices and homes.

It is a still further object of the present invention to provide an EPRD with visual and/or oral prompts that instruct the user when and for how long an emergency breath should be delivered, allowing even members of the general public without medical training to deliver highly accurate and reproducible emergency breaths.

It is yet a further object of the present invention to provide an EPRD wherein control of the delivery of an emergency breath is possible through the simple action of a finger (such as a thumb) of the user on the device. This simple action allows for highly accurate and reproducible emergency breathing to be delivered over long periods of time with little or no user fatigue. The simple action of the device also allows for the device to be inexpensively manufactured, allowing for it to be widely disseminated. Further, the simple action of the device means that it requires little maintenance, meaning it can be located in places where repair technicians are not readily available.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION OF THE INVENTION

The present invention is a emergency pulmonary resuscitation device designed (EPRD) to allow a user to easily deliver accurate and highly reproducible emergency breathing. The EPRD of the present invention preferably has simple controls that allow for control of delivery of emergency breaths through the action of a single finger. The easy and accurate control provided by the EPRD allows for consistent delivery of emergency breaths over extended periods of time without causing user fatigue.

The general term emergency breathing is used throughout this specification to describe the delivery of air to the airway of a person. Emergency breathing may be provided on its own, or as part of a standard CPR protocol, as will be described. Emergency breathing is typically required in situations where a patient is not breathing at all or not breathing normally, but there may be other situations when emergency breathing is required.

The EPRD of the present invention is configured to deliver emergency breaths in a medically accepted manner. Preferably, the EPRD is configured to deliver emergency breaths as described in the American Heart Associations CPR and Emergency Cardiac Care (ECC) Guidelines (*Circulation*, 2005: 112; IV-1-IV-203). However, the EPRD is designed so that other protocols may be followed and so that the parameters of the emergency breaths may be adjusted as protocols change.

The person to which air is being delivered may be referred to as the patient or the subject throughout this specification. The person or persons operating the EPRD may be referred to as the user(s), operator(s) or caregiver(s) throughout the specification. The user of the EPRD may be medically trained, such as a doctor, nurse or emergency medical technician. The user of the EPRD may also be a non-medically trained member of the general public who is trained in the use of the EPRD. As yet another alternative, the user of the EPRD may be a non-medically trained member of the general public who is not trained in the use of the EPRD.

The EPRD of the present invention is preferably located in places where an AED is present. As such, the EPRD of the present invention may be located in hospitals, doctors offices, emergency vehicles, homes, offices, restaurants, airports, train stations and public places. Because of the simple action of the device, it may be manufactured inexpensively in large numbers and widely disseminated. Further, the low maintenance requirements of the device allow a variety of institutions and locations to keep several on hand with low cost requirements.

Use of the EPRD of the present invention by members of the public is preferably analogous to use of an AED by members of the public. The user may be trained in the use of the device. However, if the user is not trained, the EPRD is simple enough in operation to allow it to be used by an untrained person if necessary.

Figure 1:
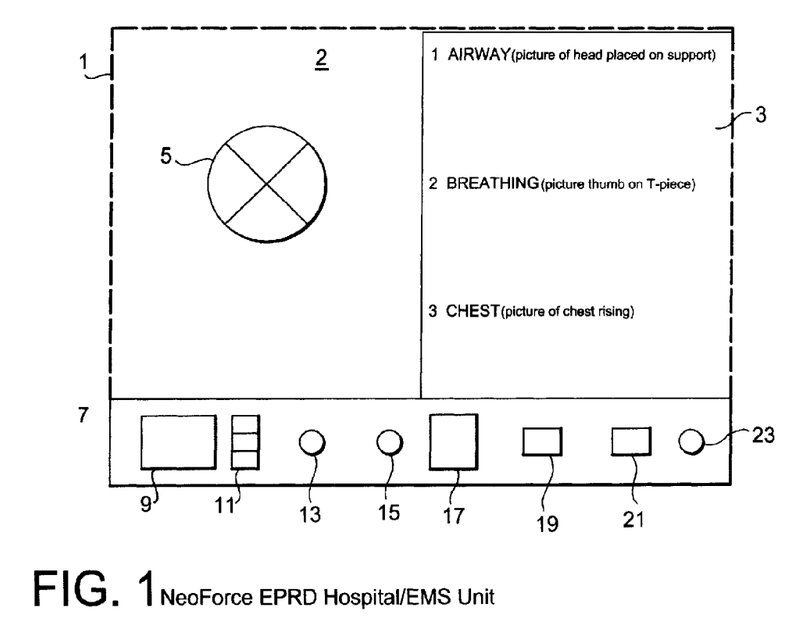
FIG. 1 shows a schematic of an embodiment of the Emergency Pulmonary Resuscitation Device (EPRD) of the present invention intended for hospital or Emergency Medical Services (EMS) use.

FIG. 1 shows a schematic of a preferred embodiment of an EPRD designed for hospital or Emergency Medical Services (EMS) use. The device is enclosed in a case 1, having a face. On one side of the face 2 of the case 1 is posted a label 3, which gives visual instructions of how to administer emergency breathing with the device. The other side of the face 2 of the case 1 may have a manometer 5, or other similar device, which measures the pressure inside the system.

Interaction with the device proceeds mainly through the user interface panel 7. The device may have a battery charge indicator 9 to indicate to the user how much of the battery charge is remaining. The device may also have a power source indicator 11 to indicate the device's current source of power. There may be a maximum pressure override button 13. Preferably, the EPRD is configured so that a maximum pressure is set by the device. However, there may be times at which is desirable for the pressure in the system to exceed this maximum pressure. When the maximum pressure override button 13 is depressed, it will allow the user to obtain a pressure above the pre-set maximum pressure value.

The device may have a gas inlet 15, wherein a source of oxygen or blended gas may be attached. The device has a start button 17 which may be depressed in order to begin its operation. The device also may have two visual indicators 19, 21, such as a green and a red indicator, that provide visual instruction to the user of the device as will be described in more detail below. Finally, the device has a patient circuit connection 23 or other similar outlet that allows for connecting of the patient circuit having a mask or endo-tracheal tube which is applied directly to the patient.

Figure 2:
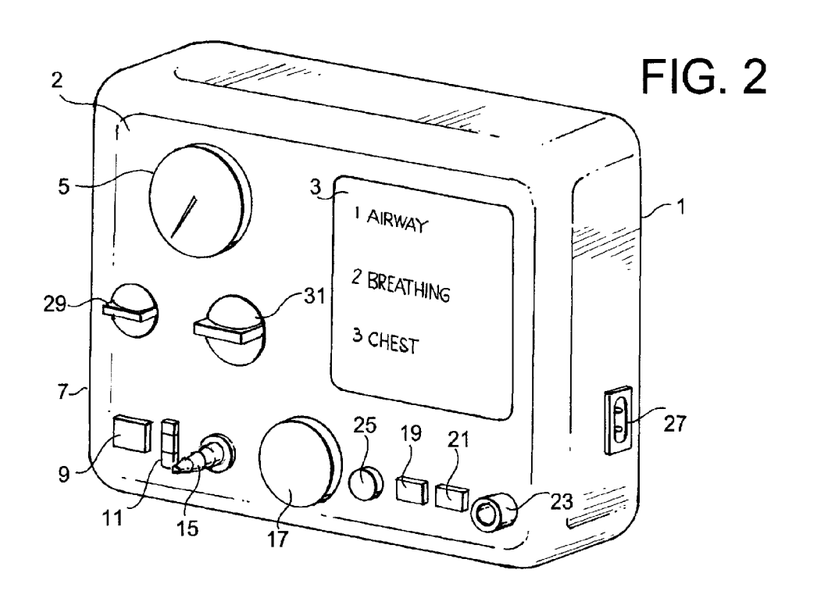
FIG. 2 shows a front view of the case of an embodiment of the EPRD of the present invention intended for hospital or Emergency Medical Services (EMS) use.

FIG. 2 shows a front view of an embodiment of an EPRD for hospital or EMS use. Components with like numbers have the same functions as those described in FIG. 1. The embodiment of FIG. 2 also includes a status indicator or "ready" light 25, that indicates whether the device is ready for use. The power source input 27 can also be seen in the view of FIG. 2. The power source input is preferably configured to receive both AC and DC sources of power. Also shown in FIG. 2 are the Maximum Pressure Relief Control (MPRC) knob 29 and the Peak Inspiratory Pressure Control (PIPC) knob 31. The MPRC knob 29 allows for an advanced user of the device to set the maximum pressure of the system, while the PIPC knob 31 allows an advanced user to set the maximum pressure which is actually delivered to the airway of the patient.

The case 1 of the EPRD of the present invention is preferably sized so that the device is highly portable and easily transported. The case may be approximately the size of a briefcase and may have handles for transporting. The case may alternatively have hooks and latches for mounting to a stationary object. The case may be made of any resilient material, such as plastic or metal. The buttons, knobs, indicators, inlets and outlets may be made of plastic, metal, glass or other suitable material.

The EPRD of the present invention preferably is able to operate on battery, DC, and AC power. The power source input 27 may be configured to receive any type of current input. The battery of the EPRD device is preferably rechargeable, but may also be disposable. Any type of suitable battery is contemplated for use with the device. The device is capable of monitoring the remaining battery lifetime, and is configured to signal to the user, such as visually through the battery charge indicator 9 or orally through an alarm or voice prompt, that the battery is nearing the end of its charge and that another source of power should be sought. The power source indicator light 11, indicates the type of power source on which the EPRD is operating. The function of the other components of the user interface 7 will be described in context of their role in the operation of the device outlined below.

Figure 3:
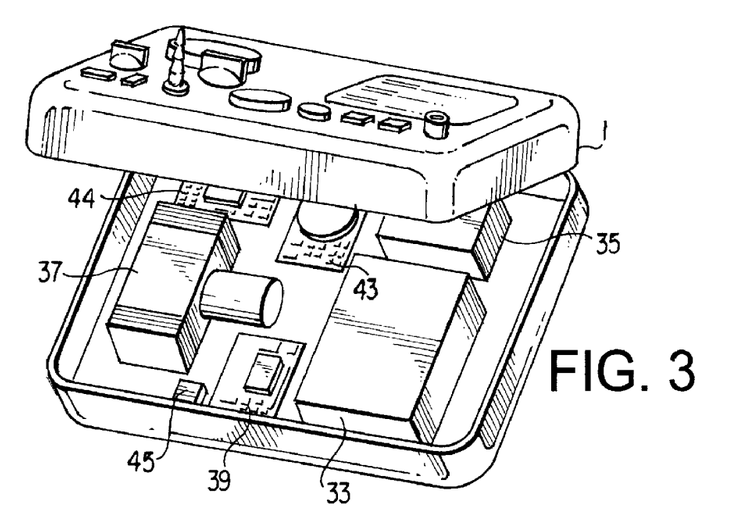
FIG. 3 shows a front view of an open case of the embodiment of FIG. 2, showing the internal components of this embodiment.

FIG. 3 shows the embodiment of the EPRD of FIG. 2 with the case 1 open, revealing the inner components of the system. The EPRD embodied in FIG. 3 has a power source 33 which receives AC or DC power through the power source input 27. The EPRD also has a battery 35, as described above. The system is driven by a pump motor 37, which causes air to flow through the system. The pump motor 37 may be any type of pump suitable for causing gasses to flow through the system and the attached circuit, such as a diaphragm pump. In alternative embodiments, the pump may be replaced with an automated baffles system, analogous to a BVM bag. The baffles system could be operated by an automatic activator capable of depressing the baffles, causing air to move through the system. In this embodiment, the activator would be calibrated to deliver a consistent volume of air in accordance with the protocol being followed by the EPRD. The baffles used in this embodiment could be similar to a bag, bellows or other device that creates a flow of air when squeezed or compressed.

The embodiment of FIG. 3 has three printed circuit boards (PCBs). The main PCB 39, is responsible for the general control of the system, controlling pump speed, battery life monitoring and such. The global positioning system (GPS) PCB 41 is responsible for operating the optional GPS. In operation, the GPS PCB 41 sends a signal that allows for location of the device by medical professionals. The GPS PCB may also be linked to a system capable of placing a 911 call, to alert medical personnel. The audio PCB 43 controls and generates the audio output of the device, as will be described. The embodiment of FIG. 3 also has a pressure sensor 45 which detects the air pressure in the system, which may be displayed on the pressure gauge 5.

Figure 4:
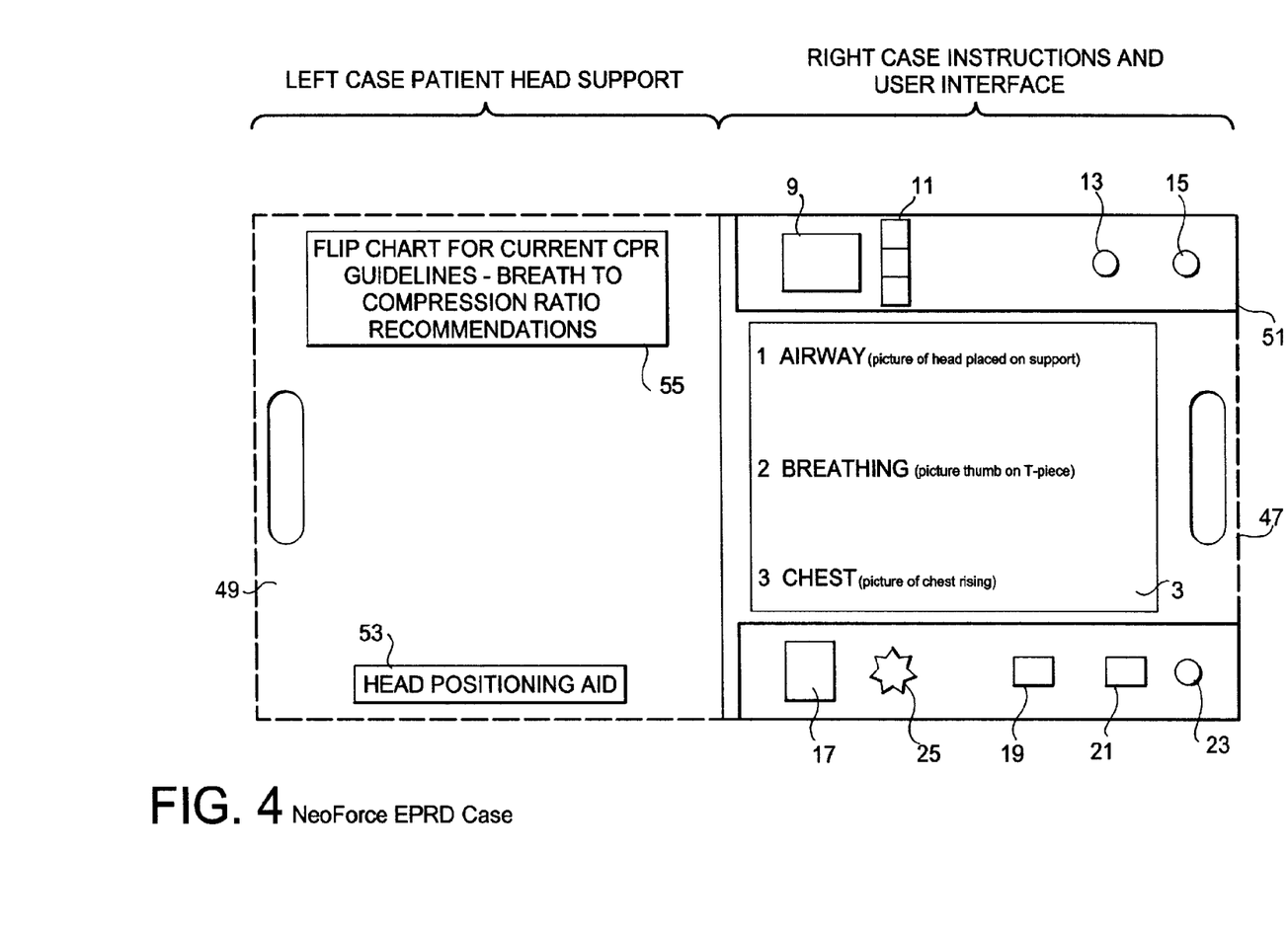
FIG. 4 shows a schematic of an embodiment of the EPRD of the present invention intended for general public use.
Figure 5:
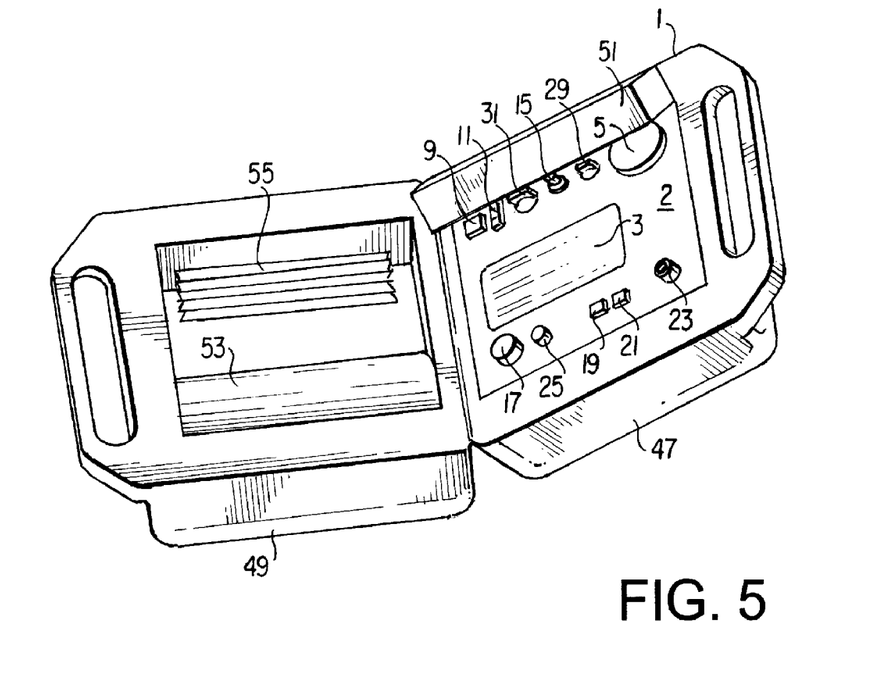
FIG. 5 shows a front view of an open case of an embodiment of the EPRD of the present invention intended for general public use.

FIGS. 4 and 5 show an alternative embodiment of the EPRD of the present invention, a device for use outside of a hospital or EMS setting. The embodiment of the FIGS. 4 and 5 has many of the same components as the hospital device, as referenced by like reference numbers. However, in this embodiment, the device is configured so the face 2 on which the user inputs are located is inside the case 1 when the case 1 is closed. In the embodiment of FIGS. 4 and 5, the case 1 of the EPRD opens up to reveal two functional sections of the device, the operator section 47 and the head positioning section 49. The operator section 47 contains the controls and indicators of the device, and is essentially like the embodiment shown in FIGS. 1-3, with modifications as will be described.

The operator section 47, as shown in FIG. 5, presents only a limited set of controls and indicators to the user upon opening of the case. Upon opening of the case, the user is presented with the face 2 of the device have the label 3, start button 17, ready indicator 25, visual indicators 19, 21, and patient circuit connection 23. The other controls and sensors, which are more typically suited for use of the device by a medical professional, may be hidden behind a panel 51. The panel may have a warning label stating that it is only to be opened by a medical professional, and/or alternatively, may be locked in some manner. When a non-medically trained member of the general public uses the device, they will only be presented with a simple, easy to understand set of controls and indicators. However, if a medically trained person were to arrive on the scene, they could then open the panel 51, allowing them access to more complicated controls and sensors.

Typically, the operator section does not easily open further to reveal the components described in FIG. 3. Instead, the general public use device described in FIGS. 4 and 5 may be sealed so that the internal components can only be accessed by an authorized serviceperson.

The head positioning section contains a head positioning aid 53. The head positioning aid 53 is preferably a pad that allows for positioning of the patient's head so that it will be in the optimal position for the administration of emergency breaths. The head positioning aid may be any type of pad or device that allows for proper positioning of the patient's head.

The head positioning section may also contain a flip chart 55 with instructions for administering emergency breathing and CPR printed thereon. The chart preferably has several pages that can be easily read and accessed. The various pages of the chart may contain continuations of previous instructions or may display the instructions in varying languages, etc.

Figure 6:
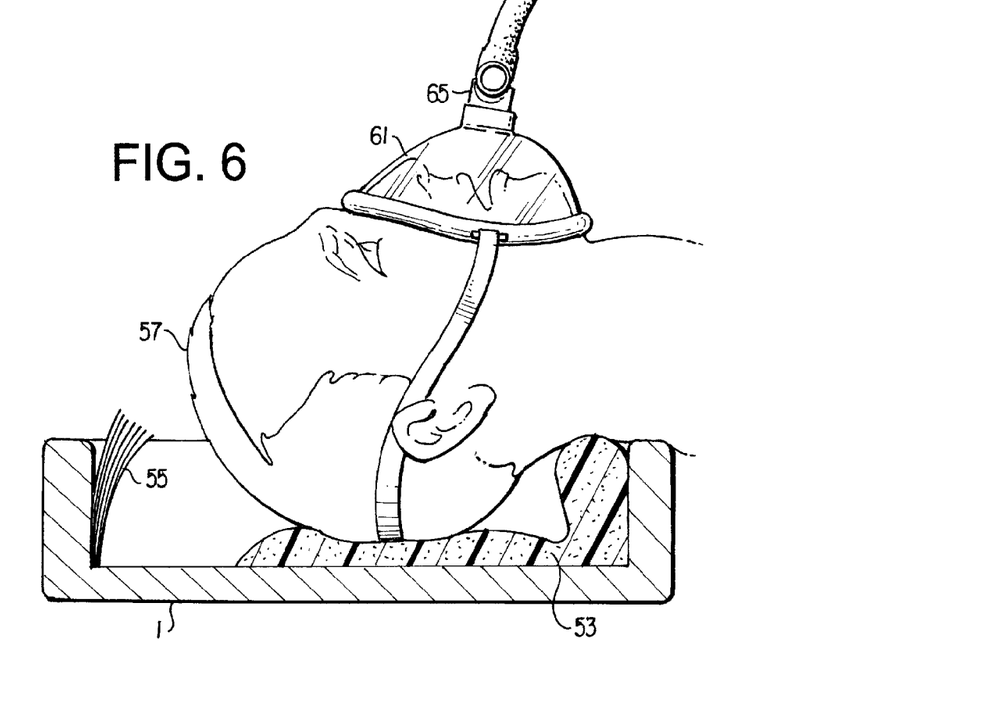
FIG. 6 shows a cut away view of the head positioning section of the embodiment of FIG. 5 with a patients head in place and wearing the patient circuit.

FIG. 6 shows a cross section of the head positioning section with a patient 57 positioned in the optimal position for an open airway. The patient 57 is shown wearing the patient circuit 59. The patient circuit has a mask 61 with an optional strap 63, and is connected to tubing (not shown in FIG. 6) through a T-piece 65. Once the patient is positioned in this manner with the mask 61 in place, emergency breathing may begin.

While FIG. 6 shows the patient positioned in the head positioning section, it is also contemplated by the invention that the patient may not be positioned in the head positioning section for delivery of emergency breaths.

Figure 7:
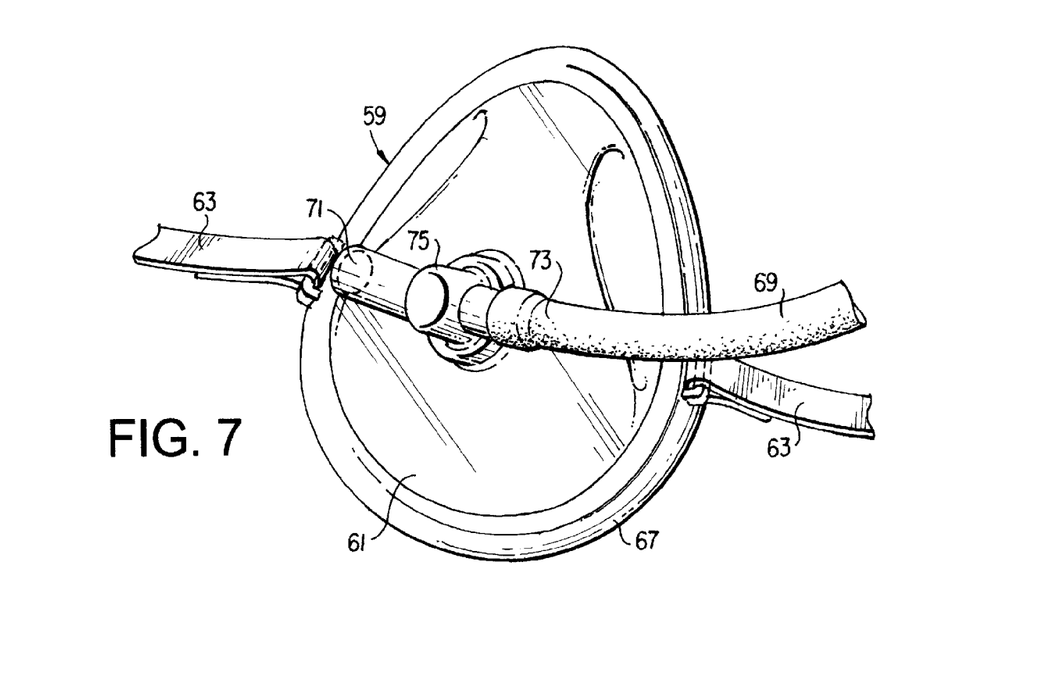
FIG. 7 shows an embodiment of the patient circuit of the present invention.
Figure 8:
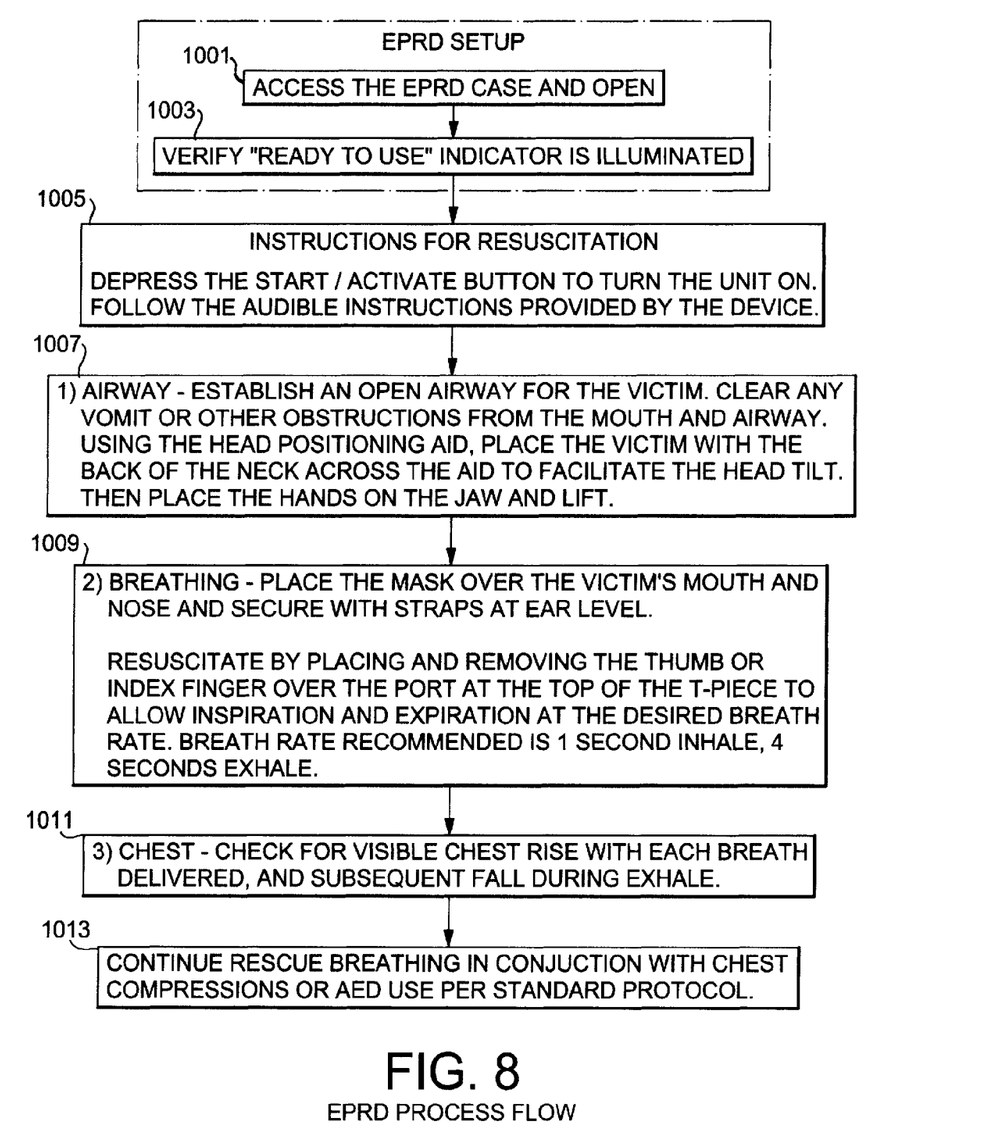
FIG. 8 is a flow diagram describing an embodiment of a process for operating the EPRD.

FIG. 7 shows an embodiment of the patient circuit 59. As described, the mask 61 has a T-piece 65. The mask 61 may be any type of mask suitable for the delivery of emergency breaths to the patient. In other embodiments of the invention, the mask may be replaced with an endo-tracheal tube or other receptacle for delivering air to the airway. The T-piece 65 has ports 71, 73, 75 which may or may not be open to atmosphere. One end of a piece of tubing 69 is attached to one of the ports 71, 73, 75 with the other end being attached to the patient circuit connection 23, on the EPRD. Preferably, only one of the ports will be left open to atmosphere. Alternatively, a valve control device may be attached, as will be described. It should be apparent to one of skill in the art that other types of pieces besides T-piece can be used with the present invention. This includes pieces of different shape with various numbers of openings and ports. Further, it should be apparent to one of skill in the art that various devices can be attached to the openings and ports of the patient circuit, such as control valves, air monitors and secondary gas sources.

Operation of the EPRD

Operation of the EPRD will now be described. Although operation of the embodiment of FIGS. 4 and 5 will be described in the context of instructions that may be provided to the user, it should be apparent that the manner of operation of the device is similar for the embodiment of the device shown in FIGS. 1-3. However, in the embodiment of the device for hospital or EMS use, the EPRD may provide fewer instructions for the user.

A flow diagram of a preferred process flow for operation of the EPRD is shown in FIG. 7. As an initial step, the EPRD is accessed and the case is opened if necessary 1001. The user should verify the ready to use indicator is illuminated signifying that the device is in a usable condition 1003. The start button 17 is depressed to activate the device 1005. The device may then give instructions audibly.

The user should then establish an open airway for the victim. Any vomit or other obstructions should be cleared from the mouth and airway. The victim should be placed with the back of the neck across the head positioning aid 53 to facilitate head tilt as shown in FIG. 5 1007. The mask 61 should be placed over the victim's mouth and nose and secured with straps 63 at ear level 1009. Resuscitation is performed by placing and removing the finger over the port at the top of the T-piece to allow inspiration and expiration at the desired breath rate. A preferred breath rate is one second for inhalation and 4 seconds for exhalation 1009. The user should check for visible chest rise during inhalation and subsequent fall during exhalation 1011. Rescue breathing can then be continued in conjunction with chest compressions or AED use per standard protocols, if necessary 1013.

The EPRD has various visible instructions available to the user. Primary among these instructions are those shown on the label 3. These instruction preferably include pictures or illustrations. For example, the airway section of the label may show a picture of a person's head position correctly for opening the airway, such as through use of the head positioning device 53. The breathing section of the label may show an illustration of the T-piece with a finger (here the thumb) in the proper position to deliver a breath. The chest section may show an illustration of a chest rising upon delivery of a breath.

The other main source of visible instruction can be found on the flip chart 55. The flip chart may include written and illustrated instructions, such as those described herein, in a variety of languages.

The EPRD may give audible instructions to help direct the user. A non-limiting example of voice instructions that may be given during the beginning of emergency breathing is as follows:

"Is the person conscious?"
"Shake and shout at the person to see if they respond."
"Call or have someone call 911."
"Airway—remove obstructions from mouth and throat.
"—place victim on their back, position aid under neck to achieve head tilt."
"—lift the jaw to fully open airway."
"Breath—place the mask over the victim's nose and mouth and secure."
"—deliver breaths by placing finger over hole and releasing."
"—8 to 10 breaths per minute."
"Chest—check for visible chest rise with each delivered breath."
"Continue breathing with chest compression."

After emergency breathing is started, every two minutes the following audible commands may repeat:

"Check patient for pulse and breath."
"Check airway."
"Continue breathing."
"Check chest rise."

It is contemplated that other audible instructions may be given by the device. As the audible commands are controlled through a PCB, the audible instructions may be easily updated and changed as necessary by updating the software of the system. Further, it is contemplated that the EPRD may provide for audible instructions in alternative languages. These languages may be selectable by the user, possibly through the control of a button or switch.

In a preferred embodiment, the EPRD of the present invention gives a set of instructions for delivering breaths. These instructions may be audible and/or visible, and are preferably both audible and visible. An audible instruction may be the sounding of a tone for the period of time in which the breath is to be delivered, or may be a voice command. An example of a voice command may be "deliver breath" at the time of breathing followed by "stop breath," when the time period for breathing has expired. Visible commands are preferably given through the visual indicators 19, 21. For example, indicator 19 may be a green light that illuminates when it is time to deliver a breath. After the period for delivering a breath has ended, indicator 21, which may be a red light, will then illuminate. If both audible and visual commands are to be used, they will be coordinated so that a user can follow either one or both of them.

When the user is commanded, either audibly or visually, they will place their finger over the opening in the T-piece. In an embodiment of the invention with a constant flow of air, this will close the breathing circuit and force air into the airway of the patient. When the EPRD signals to stop delivering the breath, the user will remove their finger to allow the patient to exhale.

It is also contemplated that the opening to the atmosphere may be fitted with an automatic valve to control breathing. The automatic valve may be coordinated with the breathing program of the system, which would cause it to close and complete the circuit to deliver a breath and then open at the end of the breathing period automatically. In this embodiment of the invention, the user is not required to use a finger to control breath delivery.

Preferably, the system has a constant flow of air, so that when the patient circuit is closed by the user, an accurate breath is delivered. It is preferable that the system have a flow rate of 600-1500 mL/s. It is most preferable that the system have a flow rate of about 1200 mL/s. This flow rate can be controlled through the main PCB, and may be adjusted as necessary. Preferably, if a breath of one second duration is being delivered, the flow rate is about 1200 mL/s, so that the patient is delivered a volume of 1200 mL per breath. In an alternative embodiment, the device has a sensor on the port open to the atmosphere to signal to the system pump to produce an airflow. In this alternative embodiment, the system does not have a constant airflow, but only produces a flow when delivery of a breath is required. This embodiment allows the pump of the device to operate less frequently, conserving system power.

In yet another embodiment of the invention, the EPRD has a baffles system instead of a pump, as described above. In this embodiment, the device has a sensor of the port open to the atmosphere to detect when the user's closes the port with their finger. The sensor will detect when the port is closed, and will signal to the activator of the baffles system to compress the baffles, causing a breath to be delivered. Upon release of the user's finger, the activator will move back to its starting position and will be ready to deliver another breath.

The EPRD is preferably capable of delivering emergency breaths from either an ambient air source, an attached source of gas, or both. If an attached source of gas is to be used, it may be attached through the gas inlet 15. Any gases that are typically used in resuscitation or respiration are contemplated for use with the EPRD. Also, it may be desirable to mix gasses with medicinal properties into the airflow of the system. This may be done by mixing the gases in the attached source of gas. Alternatively, it is contemplated that a secondary source of gas may be used. The secondary source of gas may be connected through the T-piece, to be delivered to the patient. Examples of medicinal gasses that may be used with the EPRD include, hydrogen sulfide ($H_2S$), nitric oxide, prednisone and other corticosteroids, heliox and albutrol. If a gas has a medicinal purpose but may be toxic to the user of the device upon release to the atmosphere, it is contemplated that the T-piece may contain an exhalation valve, such as those known in the art, that diverts the patients exhalant through a filter or into a closed container.

It is also contemplated that the T-piece may be fitted with a detector to detect whether or not the patient is respirating. In a preferred embodiment, the detector is a carbon dioxide detector. Examples of carbon dioxide detectors that may be used with the present invention include the STATCO2™ tidal carbon dioxide detector manufactured by KeoMed, Inc. or the CARBOCAP™ carbon dioxide detector manufactured by Vaisala Corp. If a carbon dioxide detector is used with the present invention, it may be fitted to the T-piece in a manner so that the detector receives the exhalant of the patient. The carbon dioxide detector, when present, will be used to determine if the patient is respirating and converting oxygen to carbon dioxide. The carbon dioxide detector may have a visual indicator or gauge to indicate when carbon dioxide is being exhaled. In this way, the user of the device can monitor the respiration of the patient. Alternatively, it is contemplated that the carbon dioxide detector may be operatively linked with the EPRD, providing feedback through the device. This feedback may even be linked with audible and visual indicators of the EPRD, signaling to the user when the patient is breathing.

The EPRD is preferably configured to deliver emergency breathing in a standard CPR protocol, along with chest compressions or use of an AED. If the device is to be used along with chest compressions, instructions on delivering chest compressions may be given, both audibly and/or visibly, by the EPRD. For example, after instructing the user to deliver two breaths, the EPRD may audibly instruct the user to get into position for delivering chest compressions and then may count 1 to 30, at the preferred rate of compressions.

If the EPRD is to be used with an AED, it is preferable that the EPRD be able to determine the presence of the AED, such as through the reception of a wireless signal or through the attachment of the two devices to each other with a wire. Alternatively, the EPRD can be designed with an input that allows the user to signal to the device that it will be used in conjunction with an AED. In a preferred embodiment, the EPRD is configured to be used without an AED unless an AED is detected or indicated.

If the EPRD is used in conjunction with an AED, it may use a specific software algorithm to coordinate the use of the two devices. An example of such an algorithm is diagrammed in FIG. 9. After arriving on the scene, the user checks the responsiveness of the patient as described and obtains the EPRD and AED 2001. If the patient is found to be unresponsive, the airway is opened and breathing is assessed 2003. If breathing is adequate, the person is placed in the recovery position. If not, the EPRD is applied and the patient is ventilated once every 5 to 6 seconds. The patient is then checked for a pulse 2005. If a pulse is not detected, then the patient is maintained on support breaths with continuous rechecking of the pulse 2007.

Figure 9:
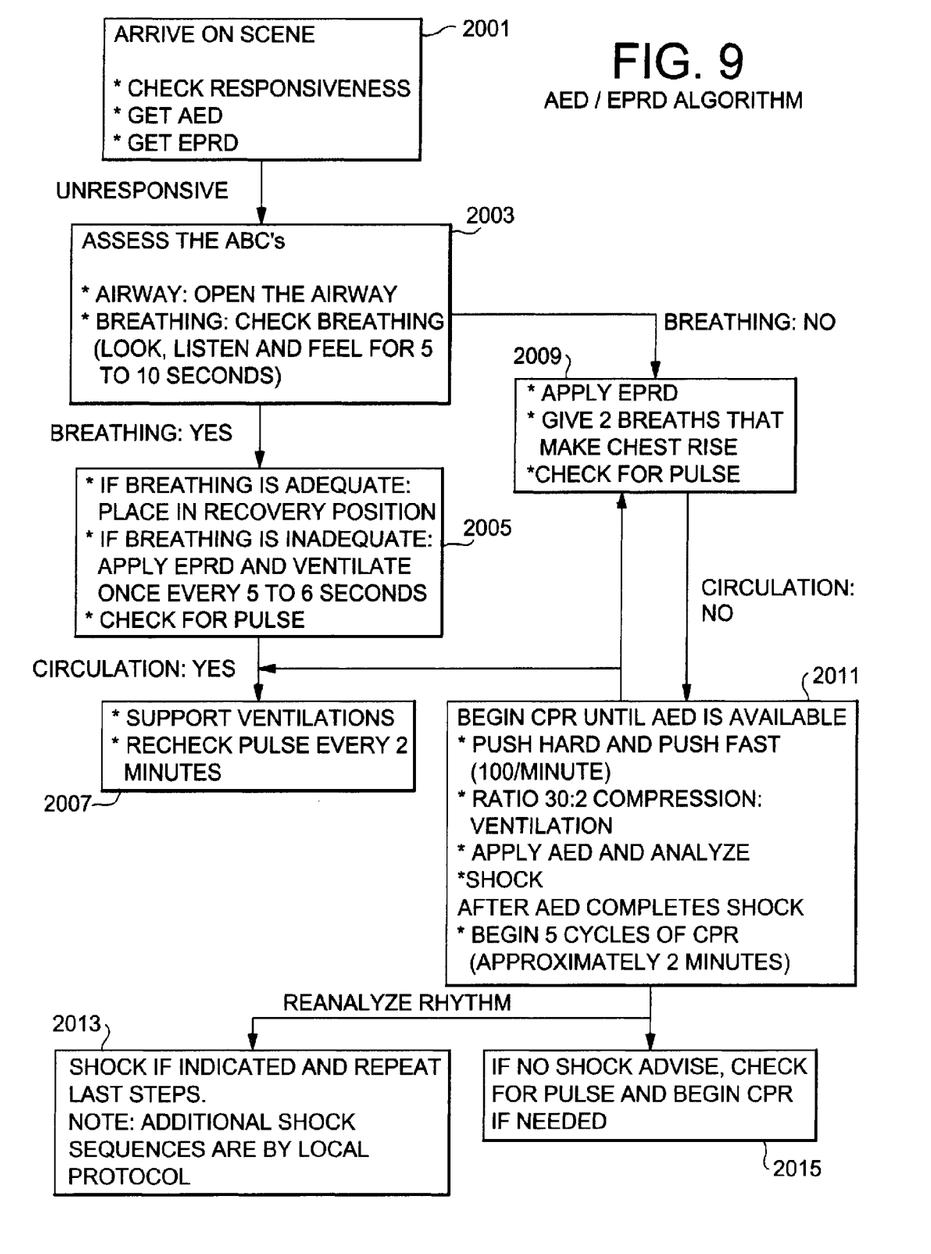
FIG. 9 is a flow diagram of an algorithm for operating the EPRD of the present invention in conjunction with an automatic external defibrillator.

If breathing is not detected, the EPRD is applied to the patient as described and 2 breaths are given. The patient's pulse is checked 2009. If the patient has no pulse, chest compressions are begun until the AED is available for use. Once the AED is available, it should be applied to the patient so that it can analyze and deliver a shock if necessary. If a shock is delivered, then 5 cycles of CPR should be delivered 2011. The AED is then used to reanalyze the heart's rhythm, and if additional shocks are necessary, they will be delivered by the local AED protocol 2013. If no additional shocks are necessary, then the patient should be checked for a pulse and CPR may be started if necessary 2015.

It is also contemplated that the EPRD of the present invention can be used in a two-person CPR protocol. The device may have a switch, accessible to medically-trained personnel, allow for the EPRD to be switched into this mode. Appropriate instructions would then be given for two-person CPR.

The operation of and instructions given by the EPRD are controlled by the various PCB's of the device. The device runs software that allows for this control. This software may be any software suitable for operating the device. Preferably, the EPRD will have a mechanism for updating the software as necessary. This may be through a wireless or wired internet connection. Software updates may be used to change the parameters of the operation of the EPRD in various ways, including those ways described above. The EPRD may also have a data card that records its use parameters for later analysis by medical personnel or technicians.

The EPRD preferably has a GPS PCB that allows for the location of the device. This GPS may be linked with a system for placing an emergency 911 call, and would allow medical personnel to locate the device in operation. Any standard GPS protocol for locating devices may be used with the EPRD.

Preferably, the EPRD has a training mode in which the GPS is not activated. This mode may be selected through a switch or other type of input.

It should be apparent to one of skill in the art that there are other variations of the EPRD which are not expressly described herein which fall within the scope and spirit of the invention as claimed below. One such variation is a device for use outside of the hospital or EMS setting (such as the embodiment of FIG. 5), without the head positioning section. The EPRD of the present invention is not meant to be limited to use with adults, but embodiments are also contemplated for pediatric and neonatal use. Further, it is contemplated that the EPRD of the present invention may be modified for use in a veterinary setting, for providing emergency breathing to companion and other animals.

What is claimed is:

1. An emergency pulmonary resuscitation device comprising:
    a compressible bag;
    an activator for compressing the compressible bag;
    a control system;
    a patient circuit receiving a flow of air, the patient circuit comprising a mask for receiving the flow of air having an opening to relieve the pressure in the system; and
    a switch operatively coupled to the activator located on the outside of the opening so that when the opening is closed, the switch is depressed;
    wherein the mask is applied to a patient in need of emergency pulmonary resuscitation, and the opening is closed for a period of time, depressing the switch and causing the activator to compress the compressible bag, causing air to flow to the system and a breath to be delivered to the patient.

2. The emergency pulmonary resuscitation device of claim 1, wherein the flow of air is from air ambient to the device.

3. The emergency pulmonary resuscitation device of claim 1, wherein the flow of air is a contained gas source.

4. The emergency pulmonary resuscitation device of claim 1, wherein the flow of air is delivered using a pump.

5. The emergency pulmonary resuscitation device of claim 4, wherein the pump is a diaphragm pump.

6. The emergency pulmonary resuscitation device of claim 1, wherein the flow of air is a constant flow of air.

7. The emergency pulmonary resuscitation device of claim 1, wherein the flow of air is an intermittent flow of air.

8. The emergency pulmonary resuscitation device of claim 1, wherein the flow of air has a flow rate of about 600-1500 mL/s.

9. The emergency pulmonary resuscitation device of claim 1, wherein the flow of air has a flow rate of about 1200 mL/s.

10. The emergency pulmonary resuscitation device of claim 1, wherein the opening is closed by the action of a finger of a user of the device.

11. The emergency pulmonary resuscitation device of claim 1, wherein the opening is closed by the action of an automatic valve.

12. The emergency pulmonary resuscitation device of claim 1, further comprising a means for providing instructions to a user controlled by the control system.

13. The emergency pulmonary resuscitation device of claim 12, wherein the instruction are instructions on how to perform emergency breathing with the device.

14. The emergency pulmonary resuscitation device of claim 12, wherein the instructions are delivered so that breaths are delivered to the patient in a manner consistent with an established CPR protocol.

15. The emergency pulmonary resuscitation device of claim 12, wherein the instruction delivered are instructions for performing CPR.

16. The emergency pulmonary resuscitation device of claim 1, wherein the control system may be synchronized with the control system of an automatic external defibrillator, wherein the emergency pulmonary resuscitation device is able to coordinate the delivery of breaths with the delivery of shocks by the automatic external defibrillator.

17. The emergency pulmonary resuscitation device of claim 16, wherein the emergency pulmonary resuscitation device and automatic external defibrillator are coordinated to deliver breaths and shocks consistent with an established CPR protocol.

18. The emergency pulmonary resuscitation device of claim 1, wherein a medicinal gas is added to the flow of air before it is delivered to the patient.

19. The emergency pulmonary resuscitation device of claim 18, wherein the medicinal gas is selected from the group consisting of:
    hydrogen sulfide, nitric oxide, corticosteroids, prednisone, heliox and albutrol.

* * * * *

UNITED STATES PATENT AND TRADEMARK OFFICE
CERTIFICATE OF CORRECTION

PATENT NO. : 7,980,244 B2  
APPLICATION NO. : 11/779037  
DATED : July 19, 2011  
INVENTOR(S) : Otho Boone et al.

Page 1 of 1

It is certified that error appears in the above-identified patent and that said Letters Patent is hereby corrected as shown below:

Title Page:

Item (73) Assignee: insert --Neoforce Innovations, LLC--; delete "Neoforce Group, Inc."

Signed and Sealed this  
Twenty-sixth Day of February, 2013

Teresa Stanek Rea  
*Acting Director of the United States Patent and Trademark Office*